US012127916B2

(12) United States Patent
Locke et al.

(10) Patent No.: US 12,127,916 B2
(45) Date of Patent: Oct. 29, 2024

(54) HIGH-DENSITY EVAPORATIVE BRIDGE DRESSING

(71) Applicant: Solventum Intellectual Properties Company, Maplewood, MN (US)

(72) Inventors: Christopher Brian Locke, Bournemouth (GB); Justin Alexander Long, Lago Vista, TX (US); Benjamin Locke, Bournemouth (GB); Benjamin Andrew Pratt, Poole (GB); Thomas Alan Edwards, Hampshire (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 16/755,814

(22) PCT Filed: Aug. 29, 2018

(86) PCT No.: PCT/US2018/048527
§ 371 (c)(1),
(2) Date: Apr. 13, 2020

(87) PCT Pub. No.: WO2019/083607
PCT Pub. Date: May 2, 2019

(65) Prior Publication Data
US 2020/0268561 A1    Aug. 27, 2020

Related U.S. Application Data

(60) Provisional application No. 62/575,983, filed on Oct. 23, 2017.

(51) Int. Cl.
*A61F 13/05*    (2024.01)
*A61F 13/00*    (2024.01)
*A61M 1/00*    (2006.01)

(52) U.S. Cl.
CPC ............. *A61F 13/05* (2024.01); *A61M 1/913* (2021.05); *A61F 2013/00246* (2013.01); *A61M 1/915* (2021.05); *A61M 1/916* (2021.05)

(58) Field of Classification Search
CPC ............ A61F 13/00068; A61F 13/0216; A61F 2013/00246; A61M 1/90
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for corresponding Application No. PCT/US2018/048527, mailed Dec. 19, 2018.

(Continued)

*Primary Examiner* — Sarah Al Hashimi
*Assistant Examiner* — Nhu Q. Tran

(57) ABSTRACT

An evaporative bridge dressing that may be used with negative-pressure treatment of tissue. The evaporative bridge dressing may have one or more fluid transfer layers comprised of high-density wicking material enclosed between layers of film having high moisture-vapor transfer rates to reduce liquid storage and minimize pressure drop.

25 Claims, 6 Drawing Sheets

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| D746,435 | S | 12/2015 | Armstrong et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2005/0101940 | A1 | 5/2005 | Radl et al. |
| 2006/0079852 | A1 | 4/2006 | Bubb et al. |
| 2007/0185463 | A1 | 8/2007 | Mulligan |
| 2008/0195017 | A1 | 8/2008 | Robinson et al. |
| 2008/0271804 | A1 | 11/2008 | Biggie et al. |
| 2008/0275409 | A1 | 11/2008 | Kane et al. |
| 2009/0221977 | A1 | 9/2009 | Blott et al. |
| 2009/0227969 | A1* | 9/2009 | Jaeb ............... A61M 1/90 604/313 |
| 2010/0137775 | A1 | 6/2010 | Hu et al. |
| 2010/0160853 | A1 | 6/2010 | Smith et al. |
| 2010/0185163 | A1 | 7/2010 | Heagle |
| 2010/0324510 | A1 | 12/2010 | Andresen et al. |
| 2010/0324516 | A1 | 12/2010 | Braga et al. |
| 2011/0230849 | A1 | 9/2011 | Coulthard et al. |
| 2012/0116334 | A1 | 5/2012 | Albert et al. |
| 2012/0215193 | A1 | 8/2012 | Siniaguine et al. |
| 2013/0066284 | A1 | 3/2013 | Croizat et al. |
| 2013/0096518 | A1 | 4/2013 | Hall et al. |
| 2013/0123722 | A1 | 5/2013 | Pratt et al. |
| 2013/0144230 | A1 | 6/2013 | Wu et al. |
| 2013/0310809 | A1 | 11/2013 | Armstrong et al. |
| 2014/0163491 | A1 | 6/2014 | Schuessler et al. |
| 2014/0276490 | A1* | 9/2014 | Locke ............... A61L 15/58 604/319 |
| 2014/0330224 | A1 | 11/2014 | Albert et al. |
| 2014/0330227 | A1* | 11/2014 | Coulthard ......... A61M 1/913 604/319 |
| 2014/0350494 | A1 | 11/2014 | Hartwell et al. |
| 2015/0080788 | A1 | 3/2015 | Blott et al. |
| 2015/0141941 | A1 | 5/2015 | Allen et al. |
| 2015/0216733 | A1 | 8/2015 | Allen et al. |
| 2015/0245950 | A1 | 9/2015 | Locke et al. |
| 2016/0106892 | A1 | 4/2016 | Hartwell |

(56) References Cited

U.S. PATENT DOCUMENTS

| | | | |
|---|---|---|---|
| 2016/0120706 A1 | 5/2016 | Collinson et al. | |
| 2016/0262942 A1 | 9/2016 | Riesinger | |
| 2016/0287765 A1 | 10/2016 | Canner et al. | |
| 2016/0339158 A1 | 11/2016 | Collinson et al. | |
| 2017/0189236 A1 | 7/2017 | Locke et al. | |
| 2018/0325741 A1 | 11/2018 | Lewis et al. | |
| 2019/0015258 A1 | 1/2019 | Gowans et al. | |
| 2019/0192350 A1 | 6/2019 | Gowans et al. | |
| 2019/0343687 A1 | 11/2019 | Locke et al. | |
| 2020/0121510 A1* | 4/2020 | Hartwell | A61F 13/0206 |
| 2021/0401628 A1 | 12/2021 | Gowans et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3195885 A1 | 7/2017 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2005051461 A1 | 6/2005 |
| WO | 2009002260 A1 | 12/2008 |
| WO | 2009089016 A1 | 7/2009 |
| WO | 2009126102 A1 | 10/2009 |
| WO | 2011087871 A2 | 7/2011 |
| WO | 2012142002 A1 | 10/2012 |
| WO | 2013/032539 A1 | 3/2013 |
| WO | 2014184674 A2 | 11/2014 |
| WO | 2015/050749 A1 | 4/2015 |
| WO | 2016126444 A1 | 8/2016 |
| WO | 2017087163 A1 | 5/2017 |
| WO | 2017196888 A1 | 11/2017 |

OTHER PUBLICATIONS

International Search Report and Written Opinion for corresponding Application No. PCT/US2018/055131, mailed Mar. 18, 2019.
International Search Report and Written Opinion for Corresponding Application No. PCT/US2019/020308, mailed May 10, 2019.
International Search Report and Written Opinion for PCT/US2017/062035, mailed Feb. 7, 2018.
International Search Report and Written Opinion for PCT/US2016/059905, mailed Jan. 26, 2017.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

(56) References Cited

OTHER PUBLICATIONS

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Japanese Notice of Rejection Corresponding to Application No. 2019-513393, mailed Aug. 3, 2021.
U.S. Non-Final Office Action Corresponding to U.S. Appl. No. 16/717,754, mailed Nov. 3, 2022.
U.S. Non-Final Office Action Corresponding to U.S. Appl. No. 16/717,609, mailed Jan. 20, 2023.
U.S. Non-Final Office Action Corresponding to U.S. Appl. No. 17/046,023, mailed Jul. 12, 2022.
Visco A, Quattrocchi A, Nocita D, Montanini R, Pistone A. Polyurethane Foams Loaded with Carbon Nanofibers for Oil Spill Recovery: Mechanical Properties under Fatigue Conditions and Selective Absorption in Oil/Water Mixtures. Nanomaterials ( Basel). p. 2.(Year: 2021).
U.S. Final Office Action Corresponding to U.S. Appl. No. 17/046,023 mailed Jan. 10, 2023.
Office Action for related U.S. Appl. No. 17/046,023, dated Jun. 7, 2024.

* cited by examiner

HIGH-DENSITY EVAPORATIVE BRIDGE DRESSING

RELATED APPLICATION

This application claims the benefit, under 35 U.S.C. § 119(e), of the filing of U.S. Provisional Patent Application Ser. No. 62/575,983, entitled "HIGH-DENSITY EVAPORATIVE BRIDGE DRESSING," filed Oct. 23, 2017, which is incorporated herein by reference for all purposes.

TECHNICAL FIELD

The invention set forth in the appended claims relates generally to tissue treatment systems and more particularly, but without limitation, to high-density evaporative bridge dressings for use with negative-pressure treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

In some embodiments, an apparatus for treating tissue with negative pressure may comprise a dressing, an evaporative fluid bridge, a fluid interface, and a fluid conductor. The apparatus may be beneficial for various modes of treatment and for various types of tissue sites, and may be particularly advantageous for use with compression bandages on shallow, highly exuding wounds, such as venous leg ulcers.

The dressing may comprise a contact layer comprised of a perforated silicone, with or without adhesive, a non-adherent polyethylene film, or ethylene-vinyl acetate mesh. The contact layer can provide adhesion and allow the dressing to be repositioned without loss of adhesion. The dressing may additionally comprise an occlusive, adhesive-coated polyurethane cover layer. One or more high-density wicking layers can be enclosed between the contact layer and the cover layer. The dressing may have no absorbent in some embodiments. The wicking layers can draw exudate and other fluid from a tissue site into the dressing and transfer the fluid to the fluid bridge. The dressing may be configured for wrapping around a limb in some embodiments. For example, some embodiments of the dressing may have flaps or wings configured to be wrapped around a leg or arm.

The fluid bridge may be fluidly coupled to the dressing. In some embodiments, the fluid bridge may comprise a lower layer of adhesive-coated polyurethane film, and a top layer of highly breathable (high MVTR) polyurethane film without an adhesive coating. One or more intermediate layers of low-profile, high-density wicking and manifolding agents may be disposed between the lower layer and the top layer. The fluid bridge preferably has no absorbent. The intermediate layers can draw fluid through the bridge toward the fluid interface. An additional intermediate layer of hydrophobic wicking material or partial layer patterned or die cut may be used to facilitate manifolding of negative pressure and transporting liquid.

The fluid interface can provide a low-profile, comfortable aperture to fluidly connect the fluid bridge to the fluid conductor, which can be fluidly coupled to a source of negative pressure. In some embodiments, the fluid interface may be manufactured from a flexible polymer, such as polyvinyl chloride (free of diethylhexyl phthalate). In some embodiments, the fluid conductor may be a tube also manufactured from a flexible polymer, such as polyvinyl chloride (free of diethylhexyl phthalate). The fluid conductor may have a single lumen in some embodiments. For example, the fluid conductor may have a single lumen with a consistent inner dimension of about 2.4 millimeters. In other embodiments, the fluid conductor may have multiple lumens, which may be suitable for use with feedback mechanisms.

In use, the dressing may be applied directly to a tissue site, and the bridge may be adhered comfortably to the dressing. Alternatively, the bridge may be adhered to the dressing before the dressing is applied to a tissue site. The fluid interface and the fluid conductor may be supplied attached or unattached to the bridge. In some treatment modes, at least some portion of the dressing, the bridge, or both may be covered by a compression means, such as a bandage or compression garment. The compression means may be hydrophobic or hydrophilic, and should be breathable so as to not prevent the exchange of air flow with the evaporative bridge. The compression means may be supplied as a component of the apparatus, or may be sourced separately.

More generally, some embodiments of an apparatus for treating a tissue site in a negative-pressure environment may comprise a dressing and a fluid transfer bridge. The dressing may comprise a tissue interface and a cover. The fluid transfer bridge may comprise an envelope having a vapor-transfer surface, a first fluid transfer layer disposed within the envelope, and a second fluid transfer layer disposed between the vapor-transfer surface and the first fluid transfer layer. The second fluid transfer layer may be disposed adjacent to the vapor-transfer surface. In some embodiments, a fluid exchange layer may be disposed between the first fluid transfer layer and the second fluid transfer layer. The tissue interface may be fluidly coupled to one end of the first fluid transfer layer in some embodiments. For example, the apparatus may comprise a fluid interface between the dressing and the fluid transfer bridge. The apparatus may additionally have a second fluid interface coupled to another end of the fluid transfer bridge opposite the tissue interface. The second fluid interface may be configured to be coupled to a fluid conductor, or may include a fluid conductor in some embodiments. The apparatus may additionally comprise a source of negative pressure, such as a pump, fluidly coupled to the fluid conductor.

In some embodiments, the envelope may comprise a polymer film having a high moisture-vapor transfer rate. For example the polymer film may be a polyurethane film having a moisture-vapor transfer rate of at least 2600 grams per square meter per twenty-four hours. In some embodiments, the envelope may comprise a base layer of polymer film coupled to a periphery of a top layer of polymer film. One or both of the first fluid transfer layer and the second fluid transfer layer may comprise a wicking member in some embodiments. For example, the first fluid transfer layer, the second fluid transfer layer, or both may comprise a textile of polyester fibers. The polyester fibers may be bonded to form a non-woven textile in some embodiments, and may have a fluid acquisition side that is hydrophilic and a fluid distribution side that is hydrophobic. In some embodiments, the fluid transfer layers may be stacked so that a fluid acquisition side is adjacent to the base layer and a fluid distribution side is adjacent to the top layer. In some embodiments, the fluid exchange layer may comprise a manifold member, such as open-cell foam.

The systems, apparatuses, and methods described herein can provide a low-profile and conformable solution for providing fluid communication with a tissue site, which may enhance patient comfort. Portable sources of negative-pressure can be used to encourage patient mobility where appropriate. Some embodiments may be optimal for 7-day wear time, and can be used with negative-pressure pumps having either integrated fluid storage or remote storage. Some embodiments can provide high evaporation rates, which can reduce the amount of fluid transferred to a container, and can the useable life of some types of negative-pressure pumps.

Some embodiments may be particularly beneficial for treating venous leg ulcers and other highly-exuding shallow wounds.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
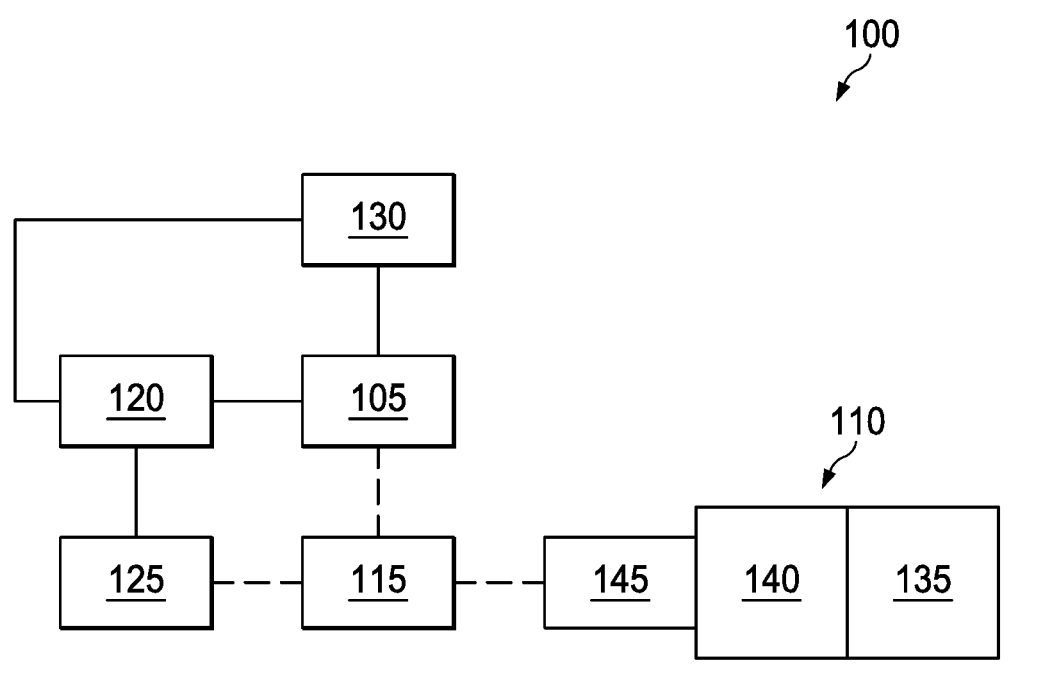
FIG. 1 is a functional block diagram of an example embodiment of a therapy system that can provide negative-pressure therapy in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, a dressing 110, a fluid container, such as a container 115, and a regulator or controller, such as a controller 120. Additionally, the therapy system 100 may include sensors to measure operating parameters and provide feedback signals to the controller 120 indicative of the operating parameters. As illustrated in FIG. 1, for example, the therapy system 100 may include a first sensor 125 and a second sensor 130, or both, coupled to the controller 120. As illustrated in the example of FIG. 1, the dressing 110 may comprise or consist essentially of a tissue interface 135, a cover 140, or both in some embodiments. A fluid bridge 145 may fluidly couple the dressing 110 to other components, such as the negative-pressure source 105.

Some components of the therapy system 100 may be housed within or used in conjunction with other components, such as processing units, alarm indicators, memory, databases, software, display devices, or user interfaces that further facilitate therapy. For example, in some embodiments, the negative-pressure source 105 may be combined with the controller 120 and other components into a therapy unit.

In general, components of the therapy system 100 may be coupled directly or indirectly. For example, the negative-pressure source 105 may be directly coupled to the container 115, and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 120, and may be fluidly coupled to one or more distribution components to provide a fluid path to a tissue site. In some embodiments, components may also be coupled by virtue of physical proximity, being integral to a single structure, or being formed from the same piece of material.

A distribution component is preferably detachable, and may be disposable, reusable, or recyclable. The dressing 110 and the container 115 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, an interface may facilitate coupling a fluid conductor to the dressing 110. For example, such an interface may be a SENSAT.R.A.C.™ Pad available from KCI of San Antonio, Texas.

A negative-pressure supply, such as the negative-pressure source 105, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy. Some examples of the therapy system 100 may include more than one container. Additionally or alternatively, the container 115 may be integrated or combined with the negative-pressure source 105 into a single unit in some embodiments.

A controller, such as the controller 120, may be a microprocessor or computer programmed to operate one or more components of the therapy system 100, such as the negative-pressure source 105. In some embodiments, for example, the controller 120 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 135, for example. The controller 120 is also preferably configured to receive one or more input signals, such as a feedback signal, and programmed to modify one or more operating parameters based on the input signals.

Sensors, such as the first sensor 125 and the second sensor 130, are generally known in the art as any apparatus operable to detect or measure a physical phenomenon or property, and generally provide a signal indicative of the phenomenon or property that is detected or measured. For example, the first sensor 125 and the second sensor 130 may be configured to measure one or more operating parameters of the therapy system 100. In some embodiments, the first sensor 125 may be a transducer configured to measure pressure in a pneumatic pathway and convert the measurement to a signal indicative of the pressure measured. In some embodiments, for example, the first sensor 125 may be a piezoresistive strain gauge. The second sensor 130 may optionally measure operating parameters of the negative-pressure source 105, such as the voltage or current, in some embodiments. Preferably, the signals from the first sensor 125 and the second sensor 130 are suitable as an input signal to the controller 120, but some signal conditioning may be appropriate in some embodiments. For example, the signal may need to be filtered or amplified before it can be processed by the controller 120. Typically, the signal is an electrical signal, but may be represented in other forms, such as an optical signal.

The tissue interface 135 can be generally adapted to partially or fully contact a tissue site. The tissue interface 135 may take many forms, and may have many sizes, shapes, or thicknesses depending on a variety of factors, such as the type of treatment being implemented or the nature and size of a tissue site. For example, the size and shape of the tissue interface 135 may be adapted to the contours of deep and irregular shaped tissue sites. Moreover, any or all of the surfaces of the tissue interface 135 may have projections or an uneven, course, or jagged profile that can induce strains and stresses on a tissue site, which can promote granulation at the tissue site.

In some embodiments, the tissue interface 135 may comprise a means to transfer fluid. For example, the tissue interface 135 may comprise or consist essentially of a fluid transfer member, such as a manifold member, a wicking member, or some combination of manifold and wicking members. A manifold member in this context generally includes material, substances, or structures that provide pathways adapted to collect or distribute fluid across a tissue site under pressure. A wicking member generally includes material, substances, or structures that can move liquid by capillary action. In some illustrative embodiments, the pathways of a manifold or wicking member may be interconnected to improve distribution or collection of fluids across a tissue site.

In some illustrative embodiments, a manifold may be a porous material having interconnected cells. For example, open-cell foam generally includes pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

Some textiles may also be suitable as a fluid transfer member. For example, woven and non-woven textiles are generally porous, making them suitable as a manifold in some embodiments. Some textiles may additionally or alternatively be configured to transfer fluid through wicking action. In general, a textile includes any cohesive network of natural or synthetic fibers. For example, fibers may be woven, knitted, knotted, pressed together, or otherwise bonded to form a textile. Sheets or webs of fibers that are bonded together by entangling fibers mechanically, thermally, or chemically are generally classified as a non-woven textile. More broadly, though, a non-woven textile may include any sheet or layer of fibers which are neither woven nor knitted, such as felt, for example.

In some embodiments, a fluid transfer member may be a composite textile having a hydrophobicity that varies from a first side to a second side. For example, the hydrophobicity may increase from an acquisition surface to a distribution surface. In some examples, a fluid transfer member may be a non-woven textile having an acquisition surface that is hydrophilic and a distribution surface that is hydrophobic. In some embodiments, a fluid distribution surface may include hydrophobic fibers oriented substantially within a plane of the surface. A fluid acquisition surface may include hydrophilic fibers oriented substantially normal to a plane of the surface. More specifically, in some example embodiments, a fluid transfer member may comprise or consist essentially of a dual-layer non-woven textile, such as a through-air bonded web of dry polyester and hydrophilic, profiled polyester and bi-component fibers. Suitable products may include the DRYWEB TDL2 acquisition and distribution layer from LIBELTEX, or the SLIMCORE TL4 acquisition and distribution layer from LIBELTEX, for example.

In some embodiments, the cover 140 may provide a bacterial barrier and protection from physical trauma. The cover 140 may also be a means for providing a fluid seal between two components or two environments, such as between a therapeutic environment and a local external environment. In some embodiments, the cover 140 may comprise or consist essentially of an occlusive material that can provide a fluid seal. The cover 140 may be, for example, an elastomeric film or membrane that can provide a seal adequate to maintain a negative pressure at a tissue site for a given negative-pressure source. The cover 140 may comprise or consist essentially of a vapor-transfer film having a high moisture-vapor transmission rate (MVTR) in some applications. For example, the MVTR of some embodiments may be at least 250 g/m^2 per twenty-four hours in some embodiments, measured by upright cup technique, according to ASTM E96/E96M Upright Cup Method at 38° C. and 10% relative humidity (RH). In some embodiments, an MVTR up to 5,000 g/m$^2$ per twenty-four hours may provide may provide effective breathability and mechanical properties. In some example embodiments, the cover 140 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 140 to an attachment surface, such as undamaged epidermis, a gasket, or another cover. The attachment device may take many forms. For example, an attachment device may be a medically-acceptable, pressure-sensitive adhesive configured to bond the cover 140 to epidermis around a tissue site. In some embodiments, for example, some or all of the cover 140 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Figure 2:
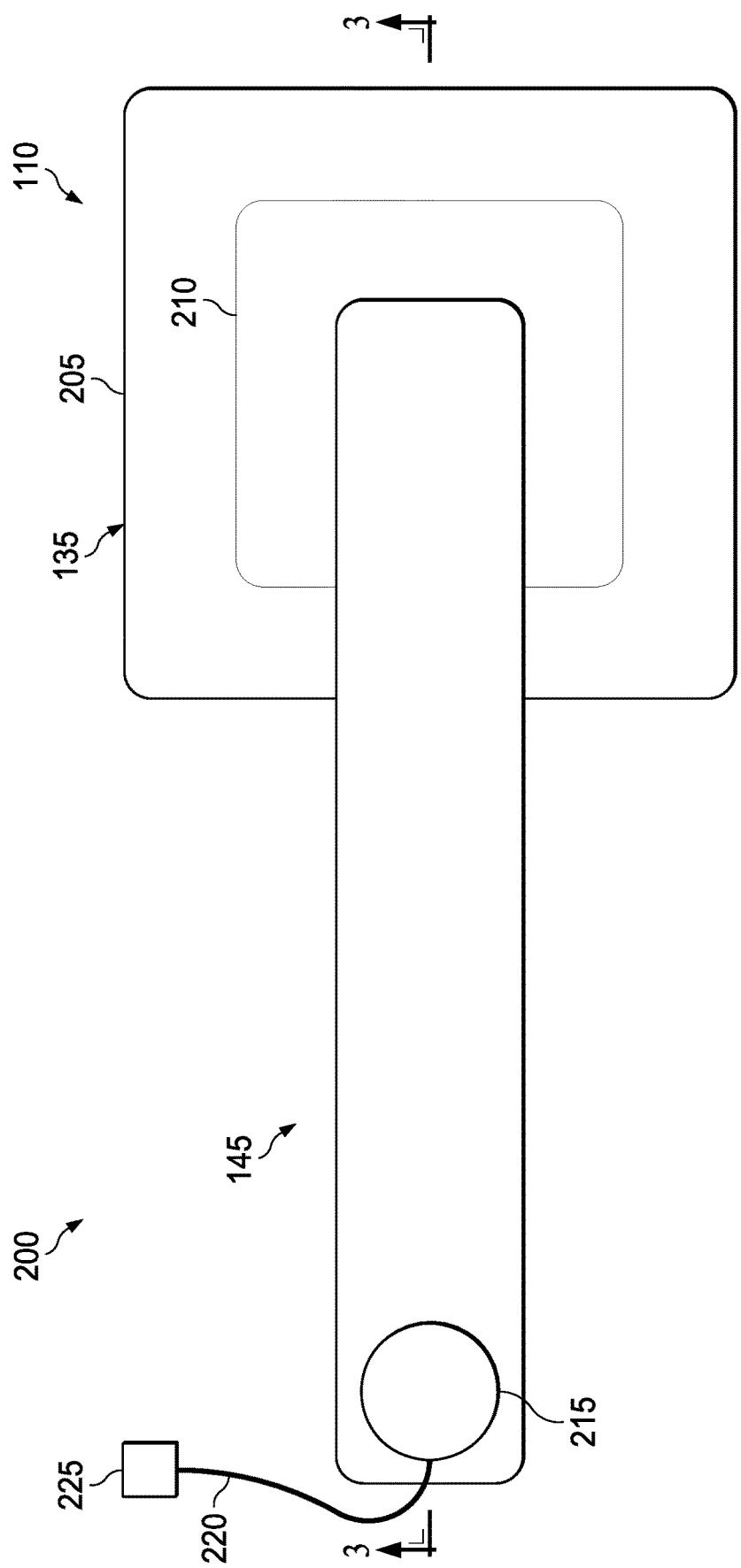
FIG. 2 is a schematic view of an example of a bridge dressing that may be associated with some embodiments of the therapy system of FIG. 1.

FIG. 2 is a schematic view of an example of a bridge dressing 200. As shown in the example of FIG. 2, the bridge dressing 200 may be an assembly of the dressing 110 and the fluid bridge 145. FIG. 2 illustrates additional details that may be associated with some examples of the dressing 110 and the fluid bridge 145. For example, the tissue interface 135 of FIG. 2 comprises a contact layer 205 and a fluid management layer 210. The fluid bridge 145 may be elongated, having a length that is substantially greater than its width. For example, the fluid bridge 145 may have an aspect ratio of about 6:1 to about 12:1. A width of about two inches and a length of about 12 to 24 inches may be suitable for some embodiments. A first end of the fluid bridge 145 may be fluidly coupled to the fluid management layer 210. A fluid interface 215 may be disposed on the second end of the fluid bridge 145. A fluid conductor 220 with a connector 225 may optionally be connected to the fluid interface 215 in some examples.

Figure 3:
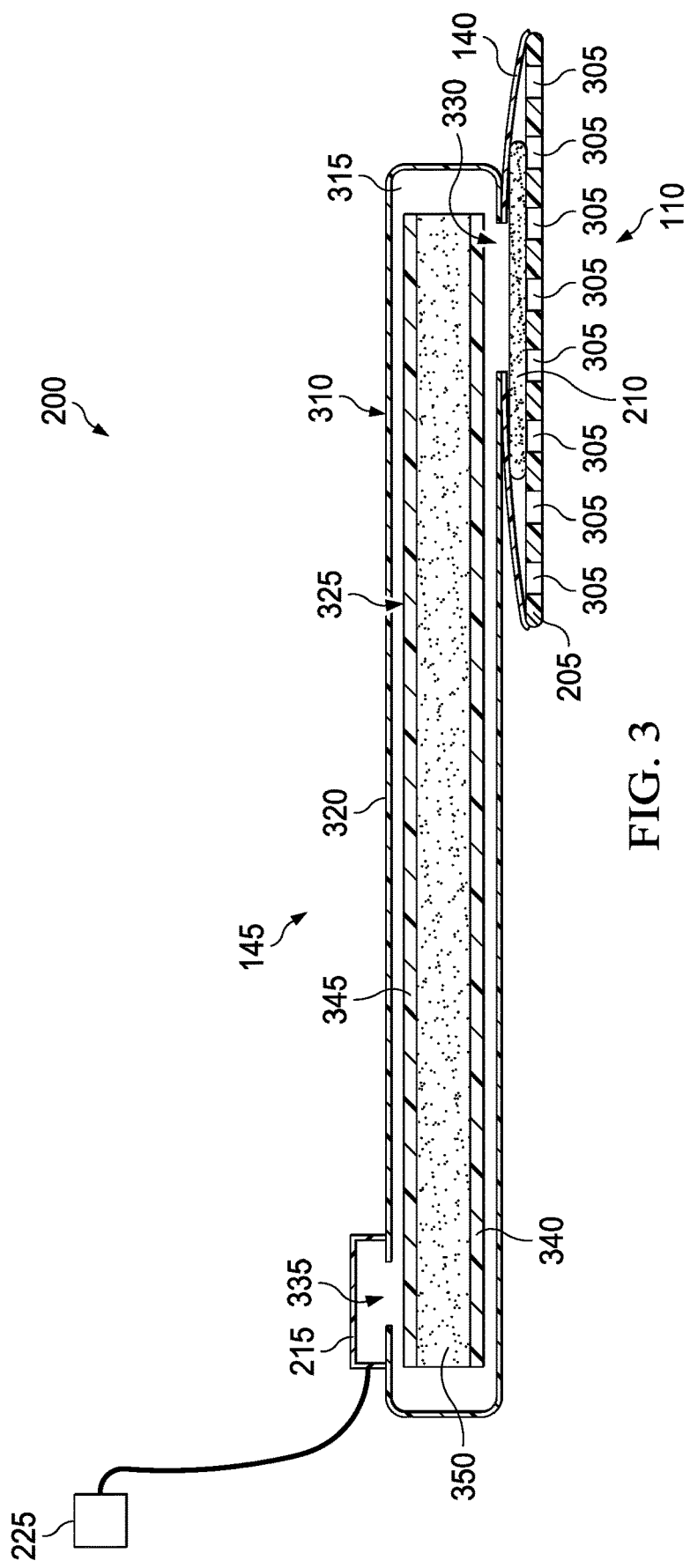
FIG. 3 is a schematic section of the bridge dressing of FIG. 2, illustrating additional details that may be associated with some embodiments.

FIG. 3 is a schematic section of the bridge dressing 200 of FIG. 2, taken along line 3-3, illustrating additional details that may be associated with some embodiments. In the example configuration of FIG. 3, the contact layer 205 has apertures 305, and the fluid management layer 210 is disposed between the cover 140 and the contact layer 205. The fluid management layer 210 can separate the cover 140 and the contact layer 205, and may comprise or consist essentially of one or more fluid transfer members. In some embodiments, the fluid management layer 210 may comprise or consist essentially of a fluid transfer layer having a fluid acquisition surface and a fluid distribution surface, such as a dual-layer non-woven textile from LIBELTEX.

The fluid bridge 145 may comprise an enclosure, such as an envelope 310, which can define a fluid channel 315. The envelope 310 may be made from a material that is impermeable to liquid, and may comprise at least one vapor-transfer surface 320 that is permeable to vapor. A fluid transfer bridge 325 may be disposed within the envelope 310, adjacent to the vapor-transfer surface 320. The fluid transfer bridge 325 may be elongated, having a length that is substantially longer than its thickness and width. In some embodiments the fluid transfer bridge 325 may substantially fill the fluid channel 315 and structurally support the envelope 310. A first end of the fluid transfer bridge 325 may be fluidly coupled to the fluid management layer 210 through a first transfer channel 330. A second end of the fluid transfer bridge 325 may be fluidly coupled to a fluid interface, such as the fluid interface 215, through a second transfer channel 335. The fluid transfer bridge 325 preferably has a low profile. A thickness of 15 millimeters or less may be suitable for some configurations.

The fluid transfer bridge 325 may comprise or consist essentially of one or more fluid transfer members, which may include one or more manifold members, wicking members, or some combination of manifold and wicking members. In FIG. 3, for example, the fluid transfer bridge 325 comprises a first wicking layer 340 and a second wicking layer 345. At least one fluid transfer layer may be disposed adjacent to the vapor-transfer surface 320 in some embodiments, and may be oriented to maximize adjacent surface area. For example, in FIG. 3 the second wicking layer 345 is disposed adjacent to the vapor-transfer surface 320. In some embodiments, the fluid transfer bridge 325 may comprise an intermediate fluid transfer member, such as an exchange layer 350. For example, the exchange layer 350 may be a hydrophilic wicking member or manifold member. The exchange layer 350 may be adapted to distribute negative pressure between the first transfer channel 330 and the second transfer channel 335, and may also be adapted to transfer liquid between the first wicking layer 340 and the second wicking layer 345.

The thickness of fluid transfer layers in the fluid transfer bridge 325 may vary according to needs of a prescribed therapy. For example, each of the first wicking layer 340 and the second wicking layer 345 may have a thickness in a range of about 1 millimeter to about 4 millimeters. A thickness in a range of about 5 millimeters to 10 millimeters may be suitable for some embodiments of the exchange layer 350, and a thickness of about 6 millimeters may be preferable. The thickness of the exchange layer 350 may be decreased to relieve stress on other layers in some embodiments. The thickness of the exchange layer 350 can also affect the conformability of the fluid transfer bridge 325.

In some embodiments, at least a portion of the first wicking layer 340 may be in direct contact with at least a portion of the second wicking layer 345. In some embodiments, at least a portion of the first wicking layer 340 may be spaced apart or separated from the second wicking layer 345 by the exchange layer 350.

One or more of the fluid transfer layers of the fluid transfer bridge 325 may have a fluid acquisition surface and a fluid distribution surface. For example, the first wicking layer 340 may have a fluid acquisition surface oriented toward the first transfer channel 330, and the second wicking layer 345 may have a fluid distribution surface oriented toward the vapor-transfer surface 320.

Figure 4:
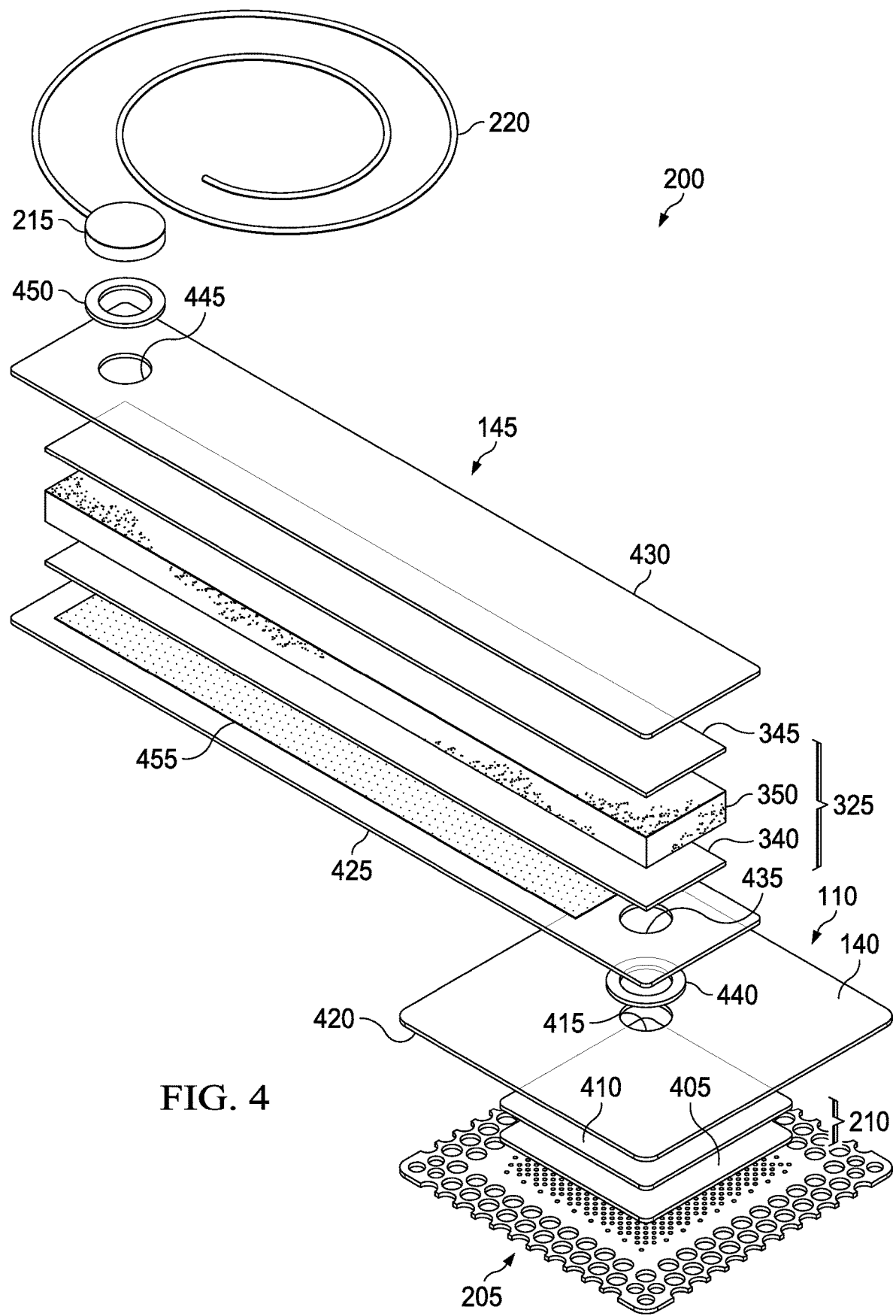
FIG. 4 is an assembly view of an example of the bridge dressing of FIG. 2, illustrating additional details that may be associated with some embodiments.

FIG. 4 is an assembly view of an example of the bridge dressing 200, illustrating additional details that may be associated with some embodiments. As illustrated in the example of FIG. 4, some embodiments of the contact layer 205 may be perforated. In some embodiments, the contact layer 205 may comprise or consist essentially of a soft, pliable material suitable for providing a fluid seal around a tissue site, and may have a substantially flat surface. For example, the contact layer 205 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the contact layer 205 may have a thickness between about 200 microns (μm) and about 1000 microns (μm). In some embodiments, the contact layer 205 may have a hardness between about 5 Shore OO and about 80 Shore OO.

In some embodiments, the contact layer 205 may be a hydrophobic-coated material. For example, the contact layer 205 may be formed by coating a spaced material, such as woven, non-woven, molded, or extruded mesh, with a hydrophobic material. The hydrophobic material for the coating may be a soft silicone, for example.

As illustrated in the example of FIG. 4, the fluid management layer 210 may comprise or consist essentially of one or more fluid transfer members, such as a third wicking layer 405 and a fourth wicking layer 410. In some examples, the third wicking layer 405 and the fourth wicking layer 410 may be disposed between the cover 140 and the contact layer 205 in a stacked relationship as shown in FIG. 4. In some examples, two or more fluid transfer layers may be laminated. For example, an adhesive or thermal weld can bond or otherwise secure the third wicking layer 405 and the fourth wicking layer 410 to each other without adversely affecting fluid transfer.

In the example of FIG. 4, the third wicking layer 405 may have a fluid acquisition surface oriented toward the contact layer 205, and the fourth wicking layer 410 may have a fluid distribution surface oriented toward the cover 140. LIBEL-TEX TDL2 having a weight of 80 gsm or similar materials may be suitable for use as or in the third wicking layer 405, the fourth wicking layer 410, or both.

In some examples, the third wicking layer 405 may have a wider base and a higher density relative to the fourth wicking layer 410. The third wicking layer 405 may have a surface area that is greater than a surface area of the fourth wicking layer 410. The third wicking layer 405 may be thicker than the fourth wicking layer 410 in some examples. For example, the third wicking layer 405 may have a thickness of about 50 millimeters, and the fourth wicking layer 410 may have a thickness of about 20 millimeters. The third wicking layer 405 may include a profile configured to spread fluid out over an entire surface of the third wicking layer 405 to increase evaporation. The fourth wicking layer 410 may be used to pull fluid away from the third wicking layer 405. In some embodiments, the fourth wicking layer 410 may alternatively or additionally include a profile like the profile of the third wicking layer 405 to spread fluid out over an entire surface of the fourth wicking layer 410. The profile of the fourth wicking layer 410 may also be used to increase evaporation.

In some embodiments, the fluid management layer 210 may include a film between two adjacent fluid transfer layers. For example, a film may be disposed between the third wicking layer 405 and the fourth wicking layer 410. The film may include one or more of the same properties as the cover 140.

The cover 140 may be coupled to the contact layer 205 to enclose the fluid management layer 210 in some embodiments. For example, the cover 140 may be adhered to a periphery of the contact layer 205 around the fluid management layer 210. In some embodiments, the cover 140 may additionally include a fluid interface such as a first aperture 415, which may be centrally disposed over the fluid management layer 210.

The cover 140 may comprise, for example, one or more of the following materials: polyurethane (PU), such as a hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polyamide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 140 may comprise INSPIRE 2301 having an MVTR (upright cup technique) of 2600 g/m$^2$/24 hours and a thickness of about 30 microns.

In the example of FIG. 4, the dressing 110 may further include an attachment device, such as an adhesive 420. The adhesive 420 may be, for example, a medically-acceptable, pressure-sensitive adhesive that extends about a periphery, a portion, or the entire cover 140. In some embodiments, for example, the adhesive 420 may be an acrylic adhesive having a coating weight between 25-65 grams per square meter (g.s.m.). Thicker adhesives, or combinations of adhesives, may be applied in some embodiments to improve the seal and reduce leaks. In some embodiments, the adhesive 420 may be continuous or discontinuous layer. Discontinuities in the adhesive 420 may be provided by apertures or holes (not shown) in the adhesive 420. The apertures or holes in the adhesive 420 may be formed after application of the adhesive 420 or by coating the adhesive 420 in patterns on a carrier layer, such as, for example, a side of the cover 140. Apertures or holes in the adhesive 420 may also be sized to enhance the moisture-vapor transfer rate of the cover 140 in some example embodiments.

In some embodiments, a release liner (not shown) may be attached to or positioned adjacent to the contact layer to protect the adhesive 420 prior to use. The release liner may also provide stiffness to assist with, for example, deployment of the dressing 110. The release liner may be, for example, a casting paper, a film, or polyethylene. Further, in some embodiments, the release liner may be a polyester material such as polyethylene terephthalate (PET), or similar polar semi-crystalline polymer. The use of a polar semi-crystalline polymer for the release liner may substantially preclude wrinkling or other deformation of the dressing 110. For example, the polar semi-crystalline polymer may be highly orientated and resistant to softening, swelling, or other deformation that may occur when brought into contact with components of the dressing 110, or when subjected to temperature or environmental variations, or sterilization. In some embodiments, the release liner may have a surface texture that may be imprinted on an adjacent layer, such as the contact layer 205. Further, a release agent may be disposed on a side of the release liner that is adjacent to the contact layer 205. For example, the release agent may be a silicone coating and may have a release factor suitable to facilitate removal of the release liner by hand and without damaging or deforming the dressing 110. In some embodiments, the release agent may be a fluorocarbon or a fluorosilicone, for example. In other embodiments, the release liner may be uncoated or otherwise used without a release agent.

As illustrated in the example of FIG. 4, the fluid bridge 145 may include a base layer 425 and a top layer 430. Each of the base layer 425 and the top layer 430 may comprise or consist essentially of a material that is substantially impermeable to liquid. The base layer 425 may include a second aperture 435, which may be disposed at one end of the base layer 425 and aligned with the first aperture 415 to form a fluid interface between the dressing 110 and the fluid bridge 145. In some embodiments, for example, the first aperture 415 and the second aperture 435 may be assembled to form the first transfer channel 330 of FIG. 3. A first adhesive ring 440 may optionally be disposed around the first aperture 415, the second aperture 435, or both in some embodiments. The top layer 430 may include a third aperture 445, which may be disposed at an end opposite the second aperture 435. In some embodiments, the third aperture 445 may be aligned with an aperture (not shown) in the fluid interface 215 to form the second transfer channel 335 of FIG. 3. A second adhesive ring 450 may optionally be disposed around the third aperture 445 in some embodiments.

The base layer 425, the top layer 430, or both may comprise or consist essentially of materials similar to the cover 140. For example, the base layer 425, the top layer 430, or both may comprise or consist essentially of a vapor-transfer film. In some embodiments, suitable materials may include a film that is permeable to vapor and substantially impermeable to liquid, and may have an MVTR in a range of about 250 grams per square meter per 24 hours and about 5000 grams per square meter per 24 hours. For example, the base layer 425, the top layer 430, or both, may comprise or consist essentially of a film having an MVTR of about 2600 grams per square meter per 24 hours. Further, in some embodiments, suitable materials may be breathable. Additional examples of suitable materials may include, without limitation, a polyurethane (PU) drape or film such as SCAPA BIOFLEX 130 polyurethane film; films formed from polymers, such as polyester and co-polyester; polyamide; polyamide/block polyether; acrylics; vinyl esters; polyvinyl alcohol copolymers; and INSPIRE 2305 polyurethane drape. High-MVTR films may be advantageous for evaporation of condensate, which may occur around the entire exterior surface of the fluid bridge 145. In this manner, capacity, fluid handling, and evaporative properties of the fluid bridge 145 may be enhanced or improved due at least to increased surface area and air movement provided around all sides and portions of the exterior surface of the fluid bridge 145.

In some examples, one or more of the fluid transfer layers of the fluid transfer bridge 325 may comprise a non-woven material or structure such as, without limitation, a polyester, co-polyester, polyolefin, cellulosic fiber, and combinations or blends of these materials. In the example of FIG. 4, the first wicking layer 340, the second wicking layer 345, or both may comprise or consist essentially of a wicking textile, such as LIBELTEX TDL2 having a weight of 80 grams per square meter or similar materials. The fluid transfer layers of the fluid transfer bridge 325 preferably have a density in a range of 0.2-0.5 grams per cubic centimeter. For example, in some embodiments, the first wicking layer 340 and the second wicking layer 345 may be a textile having a density of about 0.4 grams per cubic centimeter.

In some embodiments, the exchange layer 350 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The 25% compression load deflection of the exchange layer 350 may be at least 0.35 pounds per square inch, and the 65% compression load deflection may be at least 0.43 pounds per square inch. In some embodiments, the tensile strength of the exchange layer 350 may be at least 10 pounds per square inch. The exchange layer 350 may have a tear strength of at least 2.5 pounds per inch. In some embodiments, the exchange layer 350 may comprise or consist essentially of foam polyols such as polyester or polyether, isocyanate such as toluene diisocyanate, and polymerization modifiers such as amines and tin compounds. In some examples, the exchange layer 350 may be reticulated polyurethane ether foam having a density of about 0.2 grams per cubic centimeter.

In some embodiments, an attachment device may be disposed on an interior surface of the base layer 425, the top layer 430, or both, to secure the fluid transfer bridge 325. In some embodiments, an attachment device may be disposed between the base layer 425 and the fluid transfer bridge 325. For example, an adhesive 455 may be coated on the interior surface of the base layer 425 to adhere the first wicking layer 340 to the base layer 425. To maximize evaporation performance of the top layer 430, there may be no adhesive between the top layer 430 and the fluid transfer bridge 325 in some embodiments.

In the example of FIG. 4, the first wicking layer 340, the exchange layer 350, and the second wicking layer 345 are stacked between the base layer 425 and the top layer 430. In some embodiments, the base layer 425 and the top layer 430 may be coupled together to form the envelope 310 of FIG. 3. For example, the edges of the base layer 425 and the top layer 430 may be welded together to enclose the first wicking layer 340, the exchange layer 350, and the second wicking layer 345.

FIG. 4 also illustrates one example of the fluid interface 215 and the fluid conductor 220. As shown in the example of FIG. 4, the fluid conductor 220 may be a flexible tube, which can be fluidly coupled on one end to the fluid interface 215. The fluid interface 215 may be an elbow connector, as shown in the example of FIG. 4, which can be placed over the third aperture 445 to provide a fluid path between the fluid conductor 220 and the fluid transfer bridge 325. The fluid interface 215 may comprise or consist essentially of a soft, medical-grade polymer or other pliable material. Examples of suitable materials include polyurethane, polyethylene, polyvinyl chloride (PVC), fluorosilicone, or ethylene-propylene. In some illustrative, non-limiting embodiments, the fluid interface 215 may be molded from DEHP-free PVC. The fluid interface 215 may be formed in any suitable manner such as by molding, casting, machining, or extruding.

In some embodiments, the fluid interface 215 may be formed of a material having absorbent properties, evaporative properties, or both. The material may be vapor permeable and liquid impermeable, which can permit vapor to be absorbed into and evaporated from the material through permeation while inhibiting permeation of liquids. The absorbent material may be, for example, a hydrophilic polymer such as hydrophilic polyurethane.

Figure 5:
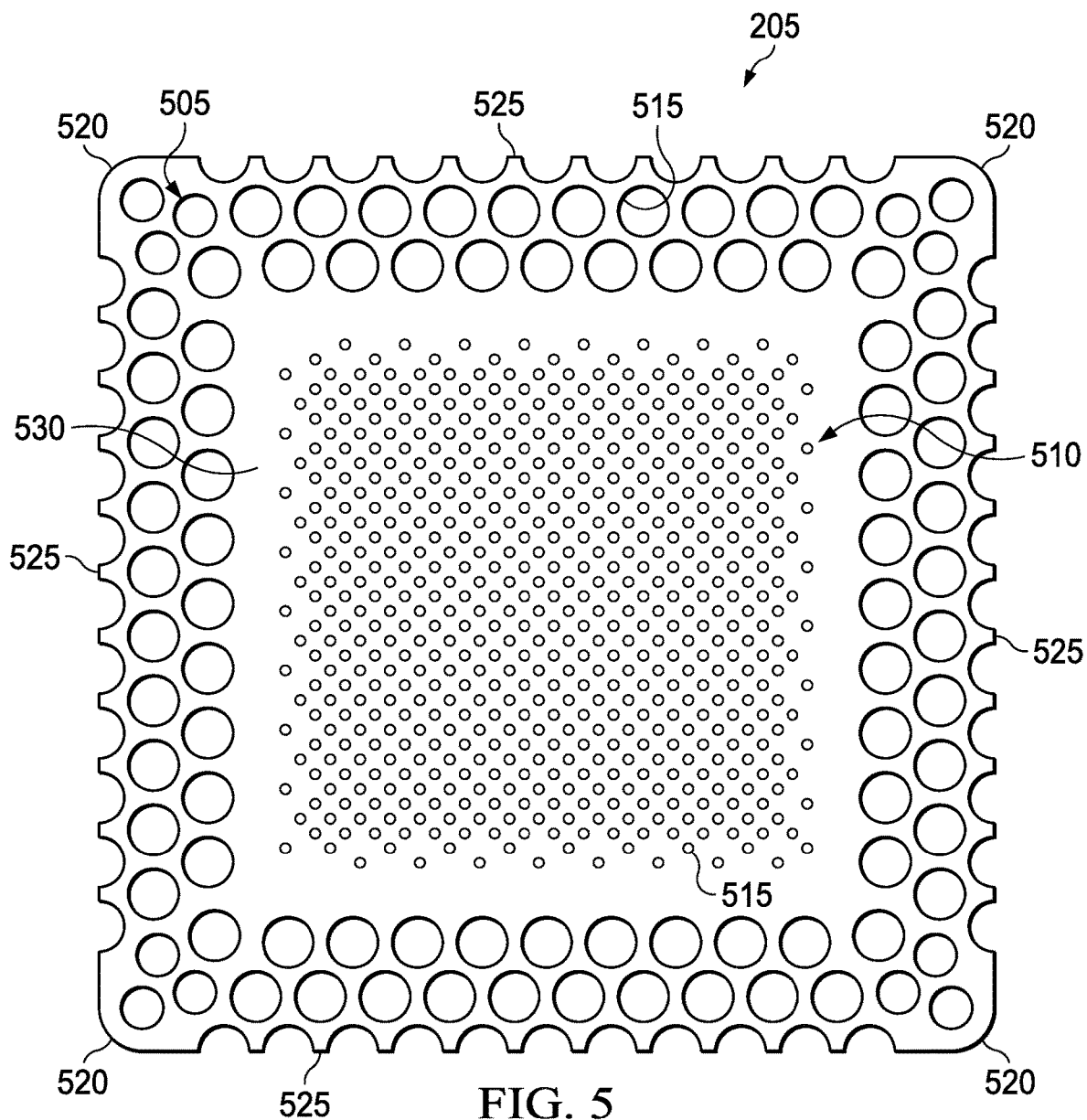
FIG. 5 is a plan view of an example contact layer that may be associated with some embodiments of the bridge dressing of FIG. 2.

FIG. 5 is a plan view of the contact layer 205 of FIG. 4, illustrating additional details that may be associated with some embodiments. For example, the contact layer 205 may have a periphery 505 surrounding or around an interior portion 510, and may have apertures 515 disposed through the periphery 505 and the interior portion 510. The interior portion 510 may correspond to a surface area of the cover 140 in some examples. The contact layer 205 may also have corners 520 and edges 525. The corners 520 and the edges 525 may be part of the periphery 505. The contact layer 205 may have an interior border 530 around the interior portion 510, disposed between the interior portion 510 and the periphery 505. The interior border 530 may be substantially free of the apertures 515, as illustrated in the example of FIG. 5. In some examples, as illustrated in FIG. 5, the interior portion 510 may be symmetrical and centrally disposed in the contact layer 205.

The apertures 515 may be formed by cutting or by application of local RF or ultrasonic energy, for example, or by other suitable techniques for forming an opening. The apertures 515 may have a uniform distribution pattern, or may be randomly distributed on the contact layer 205. The apertures 515 in the contact layer 205 may have many shapes, including circles, squares, stars, ovals, polygons, slits, complex curves, rectilinear shapes, triangles, for example, or may have some combination of such shapes.

Each of the apertures 515 may have uniform or similar geometric properties. For example, in some embodiments, each of the apertures 515 may be circular apertures, having substantially the same diameter. In some embodiments, the diameter of each of the apertures 515 may be about 1 millimeter to about 50 millimeters. In other embodiments, the diameter of each of the apertures 515 may be about 1 millimeter to about 20 millimeters.

In other embodiments, geometric properties of the apertures 515 may vary. For example, the diameter of the apertures 515 may vary depending on the position of the apertures 515 in the contact layer 205, as illustrated in FIG. 5. In some embodiments, the diameter of the apertures 515 in the periphery 505 of the contact layer 205 may be larger than the diameter of the apertures 515 in the interior portion 510 of the contact layer 205. For example, in some embodiments, the apertures 515 disposed in the periphery 505 may have a diameter between about 9.8 millimeters to about 10.2 millimeters. In some embodiments, the apertures 515 disposed in the corners 520 may have a diameter between about 7.75 millimeters to about 8.75 millimeters. In some embodiments, the apertures 515 disposed in the interior portion 510 may have a diameter between about 1.8 millimeters to about 2.2 millimeters.

At least one of the apertures 515 in the periphery 505 of the contact layer 205 may be positioned at the edges 525 of the periphery 505, and may have an interior cut open or exposed at the edges 525 that is in fluid communication in a lateral direction with the edges 525. The lateral direction may refer to a direction toward the edges 525 and in the same plane as the contact layer 205. As shown in the example of FIG. 5, the apertures 515 in the periphery 505 may be positioned proximate to or at the edges 525 and in fluid communication in a lateral direction with the edges 525. The apertures 515 positioned proximate to or at the edges 525 may be spaced substantially equidistant around the periphery 505 as shown in the example of FIG. 5. Alternatively, the spacing of the apertures 515 proximate to or at the edges 525 may be irregular.

Various components of the bridge dressing 200 may be assembled before application or in situ. For example, the cover 140 may be laminated to the fluid management layer 210, and the fluid management layer 210 may be laminated to the contact layer 205 opposite the cover 140 in some embodiments. In some embodiments, one or more layers of the dressing 110 may coextensive. For example, the contact layer 205 may be coextensive with the cover 140, as illustrated in the example of FIG. 4. In some embodiments, the dressing 110 may be provided as a single, composite dressing. For example, the contact layer 205 may be coupled to the cover 140 to enclose the fluid management layer 210, wherein the contact layer 205 is configured to face a tissue site. Additionally or alternatively, the fluid bridge 145 may be provided as a composite structure, and may be provided attached or unattached to the dressing 110.

In use, the release liner (if included) may be removed to expose the contact layer 205, which may be placed within, over, on, or otherwise proximate to a tissue site. The contact layer 205 may be sufficiently tacky to hold the dressing 110 in position, while also allowing the dressing 110 to be removed or re-positioned without trauma to a tissue site.

Removing the release liner can also expose adhesive, such as the adhesive 420, and the cover 140 may be attached to an attachment surface. For example, the cover 140 may be attached to epidermis peripheral to a tissue site, around the fluid management layer 210. In the example of FIG. 5, the adhesive 420 may be in fluid communication with an attachment surface through the apertures 515 in at least the periphery 505 of the contact layer 205. The adhesive 420 may also be in fluid communication with the edges 525 through the apertures 515 exposed at the edges 525.

Once the dressing 110 is in a desired position, the adhesive 420 may be pressed through the apertures 515 to bond the dressing 110 to the attachment surface. The apertures 515 at the edges 525 may permit the adhesive 420 to flow around the edges 525 for enhancing the adhesion of the edges 525 to an attachment surface.

In some embodiments, apertures or holes in the contact layer 205 may be sized to control the amount of the adhesive 420 in fluid communication with the apertures 515. For a given geometry of the corners 520, the relative sizes of the apertures 515 may be configured to maximize the surface area of the adhesive 420 exposed and in fluid communication through the apertures 515 at the corners 520. For example, as shown in FIG. 5, the edges 525 may intersect at a substantially right angle, or about 90 degrees, to define the corners 520. In some embodiments, the corners 520 may have a radius of about 10 millimeters. Further, in some embodiments, three of the apertures 515 having a diameter between about 7.75 millimeters to about 8.75 millimeters may be positioned in a triangular configuration at the corners 520 to maximize the exposed surface area for the adhesive 420. In other embodiments, the size and number of the apertures 515 in the corners 520 may be adjusted as necessary, depending on the chosen geometry of the corners 520, to maximize the exposed surface area of the adhesive 420. Further, the apertures 515 at the corners 520 may be fully housed within the contact layer 205, substantially precluding fluid communication in a lateral direction exterior to the corners 520. The apertures 515 at the corners 520 being fully housed within the contact layer 205 may substantially preclude fluid communication of the adhesive 420 exterior to the corners 520, and may provide improved handling of the dressing 110 during deployment at a tissue site. Further, the exterior of the corners 520 being substantially free of the adhesive 420 may increase the flexibility of the corners 520 to enhance comfort.

In some embodiments, the bond strength of the adhesive 420 may vary in different locations of the dressing 110. For example, the adhesive 420 may have lower bond strength in locations adjacent to the contact layer 205 where the apertures 515 are relatively larger, and may have higher bond strength where the apertures 515 are smaller. Adhesive 420 with lower bond strength in combination with larger apertures 515 may provide a bond comparable to adhesive 420 with higher bond strength in locations having smaller apertures 515.

The fluid bridge 145 may be fluidly coupled to the dressing 110, if appropriate, and the fluid bridge 145 may be fluidly coupled to the negative-pressure source 105. In some embodiments, the fluid bridge 145 may be coupled to the negative-pressure source 105 through the fluid interface 215. For example, if not already configured, the fluid interface 215 may be disposed over the third aperture 445 and attached to the fluid bridge 145. The fluid conductor 220 may be fluidly coupled to the fluid interface 215 and to the negative-pressure source 105.

Thus, the dressing 110 can provide a sealed therapeutic environment proximate to a tissue site, substantially isolated from the external environment, and the negative-pressure source 105 can reduce the pressure in the sealed therapeutic environment. The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

Negative pressure applied through the dressing 110 across a tissue site in a sealed therapeutic environment can induce macrostrain and micro-strain in the tissue site, as well as remove exudates and other fluids from the tissue site, which can be collected in the container 115. The fluid management layer 210 can preference exudate and other fluid away from a tissue site and substantially prevent fluid from returning to the tissue site. Liquid exudate may be at least partially evaporated as it moves through the fluid bridge 145, decreasing the volume of liquid collected in the container 115.

The contact layer 205 may provide an effective and reliable seal against challenging anatomical surfaces, such as an elbow or heel, at and around a tissue site. Further, the dressing 110 may permit re-application or re-positioning, to correct air leaks caused by creases and other discontinuities between the dressing 110 and a tissue site. The ability to rectify leaks may increase the efficacy of the therapy and reduce power consumption in some embodiments.

In some applications, a filler may also be disposed between a tissue site and the contact layer 205. For example, if the tissue site is a surface wound, a wound filler may be applied interior to the periwound, and the contact layer 205 may be disposed over the periwound and the wound filler. In some embodiments, the filler may be a manifold, such as open-cell foam.

Additionally or alternatively, compression may be applied to portions of the bridge dressing 200 in some treatment applications. For example, the bridge dressing 200 may be placed on a wound, and breathable bandages or compression garments may be placed over at least portions of the bridge dressing 200 in some embodiments.

The systems, apparatuses, and methods described herein may provide significant advantages. For example, the bridge dressing 200 can provide a low-profile and conformable solution for providing fluid communication with a tissue site, which may enhance patient comfort. The bridge dressing 200 may be used with a portable source of negative-pressure to encourage patient mobility where appropriate. Some embodiments of the bridge dressing 200 may be optimized for 7-day wear time, and can be used with negative-pressure pumps having either integrated fluid storage or remote storage.

Higher-density materials within the bridge dressing 200 can reduce the amount of dead air space in the therapy system 100, which can be particularly beneficial for manual pumps and low-power sources of negative pressure. For example, reducing dead air space can reduce draw-down times. Additionally, some manual pumps may have integrated fluid storage and cannot be recharged once the fluid reaches storage capacity. The bridge dressing 200 can provide high evaporation rates, which can reduce the amount of fluid transferred to a container and extend the useable life of the pump.

Figure 6:
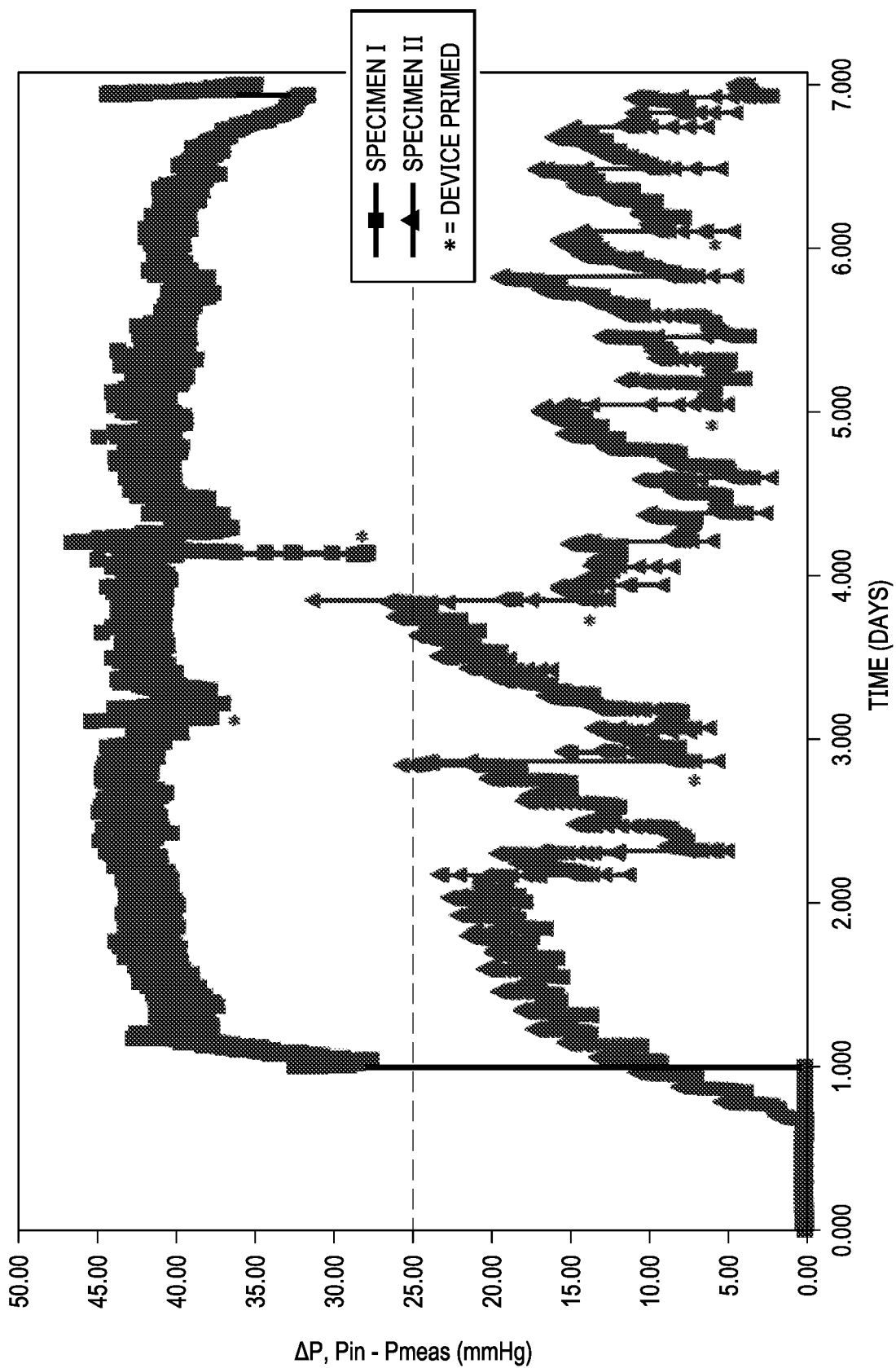
FIG. 6 is a chart illustrative of pressure drop performance that may be associated with some features of the bridge dressing of FIG. 2.

The bridge dressing 200 can also minimize pressure drops between a negative-pressure source and a tissue site. FIG. 6 is illustrative of pressure drop performance that may be associated with some features of the bridge dressing 200. FIG. 6 represents pressure data collected over a period of 7 days from two specimens. Specimen I included a dressing coupled to a manual pump with integrated fluid storage. A tube was used to fluidly couple the dressing of Specimen I to the manual pump. Specimen I did not have a bridge. Specimen II included a dressing with an evaporative bridge fluidly coupled to the same type of manual pump with integrated fluid storage. As evidenced by FIG. 6, Specimen II maintained a pressure drop over the period that was generally less than 25 mmHg, substantially less than the pressure drop maintained by Specimen I.

The bridge dressing 200 may be particularly beneficial for treating venous leg ulcers. A venous leg ulcer is a specialized wound that typically occurs on the lower leg, just above the ankle. An ulcer can take anywhere from four to six weeks to heal with current treatment options. Treating a venous leg ulcer with negative pressure may control exudate, encourage blood flow, and promote healing. Combined with a portable source of negative pressure, the bridge dressing 200 can extend times between dressing changes, and allow a patient to remain ambulatory between dressing changes. Patient mobility is often encouraged during treatment to prevent additional patient comorbidities.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 120 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for managing fluid from a tissue site, the apparatus comprising:
 a dressing comprising a tissue interface and a cover;
 a fluid transfer bridge comprising:
  an envelope having a vapor-transfer surface,
  a first fluid transfer layer disposed within the envelope,
  a second fluid transfer layer disposed within the envelope adjacent to the vapor-transfer surface,
  an attachment device disposed between the first fluid transfer layer and the envelope, the attachment device configured to couple the first fluid transfer layer to the envelope, and
  a fluid exchange layer comprising a reticulated foam disposed between the first fluid transfer layer and the second fluid transfer layer, the fluid exchange layer coextensive with and having surfaces in contact with the first fluid transfer layer and the second fluid transfer layer, the fluid exchange layer configured to transfer liquid between the first fluid transfer layer and the second fluid transfer layer; and
 a fluid interface between the dressing and the fluid transfer bridge, the fluid interface fluidly coupling the tissue interface to the first fluid transfer layer.

2. The apparatus of claim 1, wherein the envelope comprises a polyurethane film having a moisture-vapor transfer rate of at least 2600 grams per square meter per twenty-four hours.

3. The apparatus of claim 1, wherein:
 the first fluid transfer layer comprises a first wicking member; and
 the second fluid transfer layer comprises a second wicking member.

4. The apparatus of claim 1, wherein:
 the vapor-transfer surface has a moister-vapor transfer rate of at least 2600 grams per square meter per twenty-four hours;
 the first fluid transfer layer comprises a first wicking member; and
 the second fluid transfer layer comprises a second wicking member.

5. The apparatus of claim 1, wherein:
 the first fluid transfer layer has a fluid acquisition surface oriented toward the fluid interface;
 the second fluid transfer layer has a fluid distribution surface facing the vapor-transfer surface; and
 the fluid exchange layer is configured to transfer liquid between the first fluid transfer layer and the second fluid transfer layer.

6. The apparatus of claim 1, wherein:
 the vapor-transfer surface comprises a polyurethane film having a moister-vapor transfer rate of at least 2600 grams per square meter per twenty-four hours;
 the first fluid transfer layer has a fluid acquisition surface oriented toward the fluid interface;
 the second fluid transfer layer has a fluid distribution surface facing the vapor-transfer surface; and
 the fluid exchange layer is configured to transfer liquid between the first fluid transfer layer and the second fluid transfer layer.

7. The apparatus of claim 1, wherein:
 the vapor-transfer surface comprises a polyurethane film having a moister-vapor transfer rate of at least 2600 grams per square meter per twenty-four hours;
 the first fluid transfer layer and the second fluid transfer layer each comprise a dual-layer non-woven textile having a fluid acquisition surface and a fluid distribution surface; and
 the fluid exchange layer is configured to transfer liquid between the first fluid transfer layer and the second fluid transfer layer.

8. The apparatus of claim 1, wherein:
 the vapor-transfer surface comprises a polyurethane film having a moister-vapor transfer rate of at least 2600 grams per square meter per twenty-four hours; and
 the first fluid transfer layer and the second fluid transfer layer each comprise a dual-layer non-woven textile having a fluid acquisition surface and a fluid distribution surface.

9. The apparatus of claim 1, wherein a portion of the first fluid transfer layer is in contact with the second fluid transfer layer.

10. The apparatus of claim 1, wherein the tissue interface comprises a contact layer and a fluid management layer.

11. The apparatus of claim 10, wherein the contact layer is perforated.

12. The apparatus of claim 10, wherein the contact layer is configured to provide a seal around a tissue site.

13. The apparatus of claim 10, wherein the contact layer comprises perforated silicone.

14. The apparatus of claim 10, wherein the contact layer is perforated and is comprised of a material selected from a group consisting of: a silicone gel, a soft silicone, hydrocolloid, hydrogel, polyurethane gel, polyolefin gel, hydrogenated styrenic copolymer gel, a foamed gel, a soft closed cell foam coated with an adhesive, polyurethane, polyolefin, and hydrogenated styrenic copolymers.

15. The apparatus of claim 10, wherein the fluid management layer comprises a fluid transfer layer.

16. The apparatus of claim 10, wherein the fluid management layer comprises a third wicking member.

17. The apparatus of claim 10, wherein the fluid management layer comprises a third wicking member having a fluid acquisition surface oriented toward the contact layer and a fluid distribution surface oriented toward the cover.

18. The apparatus of claim 10, wherein the envelope comprises a base layer and a top layer coupled to a periphery of the base layer.

19. The apparatus of claim 1, wherein the fluid transfer bridge has a thickness less than 15 millimeters.

20. The apparatus of claim 1, wherein the first fluid transfer layer and the second fluid transfer layer each have a thickness in a range of about 1 millimeter to about 4 millimeters.

21. The apparatus of claim 1, wherein the fluid exchange layer has a thickness in a range of about 5 millimeters to about 10 millimeters.

22. The apparatus of claim 1, further comprising a negative-pressure source fluidly coupled to the fluid transfer bridge.

23. The apparatus of claim 22, wherein the negative-pressure source is manually-actuated.

24. The apparatus of claim 23, further comprising a fluid container integrally coupled to the negative-pressure source.

25. The apparatus of claim 1, wherein there is no external fluid container.

* * * * *